United States Patent
Yachi et al.

(10) Patent No.: US 10,125,201 B2
(45) Date of Patent: Nov. 13, 2018

(54) POLYOLEFIN RESIN FOAM SHEET AND ADHESIVE TAPE

(71) Applicant: SEKISUI CHEMICAL CO., LTD., Osaka (JP)

(72) Inventors: Koji Yachi, Shiraoka (JP); Shigeki Matsuki, Hikone (JP); Asami Matsumoto, Hasuda (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/514,093

(22) PCT Filed: Sep. 29, 2015

(86) PCT No.: PCT/JP2015/077600
§ 371 (c)(1),
(2) Date: Mar. 24, 2017

(87) PCT Pub. No.: WO2016/052557
PCT Pub. Date: Apr. 7, 2016

(65) Prior Publication Data
US 2017/0291968 A1    Oct. 12, 2017

(30) Foreign Application Priority Data

Sep. 30, 2014  (JP) ................. 2014-202146
Mar. 25, 2015  (JP) ................. 2015-063308

(51) Int. Cl.
| | | |
|---|---|---|
| C08J 9/35 | (2006.01) | |
| C08F 10/02 | (2006.01) | |
| C08J 9/06 | (2006.01) | |
| C08F 4/6192 | (2006.01) | |
| G01N 25/48 | (2006.01) | |
| C08J 9/00 | (2006.01) | |
| C08J 9/10 | (2006.01) | |
| C09J 7/20 | (2018.01) | |
| C09J 7/38 | (2018.01) | |

(52) U.S. Cl.
CPC .......... *C08F 10/02* (2013.01); *C08F 4/61922* (2013.01); *C08J 9/0061* (2013.01); *C08J 9/06* (2013.01); *C08J 9/103* (2013.01); *C08J 9/35* (2013.01); *C09J 7/20* (2018.01); *C09J 7/381* (2018.01); *G01N 25/4866* (2013.01); *C08J 2201/026* (2013.01); *C08J 2201/03* (2013.01); *C08J 2205/044* (2013.01); *C08J 2207/02* (2013.01); *C08J 2303/04* (2013.01); *C08J 2323/06* (2013.01); *C08J 2423/06* (2013.01)

(58) Field of Classification Search
CPC ......... C08F 10/02; C08F 4/61922; C08J 9/35; C09J 7/021
See application file for complete search history.

(56) References Cited

U.S. PATENT DOCUMENTS

| | | | |
|---|---|---|---|
| 7,291,382 B2 * | 11/2007 | Krueger | A61L 15/225 428/304.4 |
| 2006/0177642 A1 * | 8/2006 | Tateo | C08J 9/06 428/304.4 |
| 2013/0344311 A1 | 12/2013 | Yoshioka et al. | |
| 2016/0194471 A1 * | 7/2016 | Yachi | C09J 201/00 428/220 |
| 2017/0292002 A1 * | 10/2017 | Matsuki | C08J 9/103 |

FOREIGN PATENT DOCUMENTS

| | | |
|---|---|---|
| CN | 103415558 | 11/2013 |
| JP | 2012-214626 | 11/2012 |
| JP | 2014-28925 | 2/2014 |
| WO | 2013/099755 | 7/2013 |
| WO | 2013/191106 | 12/2013 |

OTHER PUBLICATIONS

International Search Report dated Jan. 12, 2016 in Inetnerational (PCT) Application No. PCT/JP2015/077600.

* cited by examiner

*Primary Examiner* — Hannah J Pak
(74) *Attorney, Agent, or Firm* — Wenderoth, Lind & Ponack, L.L.P.

(57) ABSTRACT

There is provided a polyolefin resin foam sheet having a plurality of cells which is formed by foaming a polyolefin resin composition, wherein the polyolefin resin composition contains a polyolefin resin (A) having relatively high density and a polyolefin resin (B) having relatively low density, and the weighted average resin density of the polyolefin resin (A) and the polyolefin resin (B) is 0.900 g/cm$^3$ or less; and wherein a ratio [TD strength at break/MD maximum cell size] and a ratio [MD strength at break/TD maximum cell size] are both 45 kPa/μm or more.

6 Claims, 1 Drawing Sheet

POLYOLEFIN RESIN FOAM SHEET AND ADHESIVE TAPE

TECHNICAL FIELD

The present invention relates to a polyolefin resin foam sheet obtained by foaming a polyolefin resin, particularly to a polyolefin resin foam sheet suitable as an impact absorber and an adhesive tape using the same.

BACKGROUND ART

Since a resin foam sheet in which a large number of cells are formed in the inner part of a resin layer is excellent in cushioning properties, it is widely used as an impact absorber of various electric equipment, and the like. The impact absorber is arranged and used between a glass plate and an image display member which constitute a device surface in a display device used, for example, for a mobile phone, a personal computer, electronic paper, and the like. A polyolefin resin foam sheet is known as a resin foam sheet used for such applications (for example, refer to Patent Literatures 1 and 2).

CITATION LIST

Patent Literature

PTL1: JP 2014-028925 A
PTL2: WO 2013/099755

SUMMARY OF INVENTION

Technical Problem

In recent years, the electronic equipment used in the information technology field has been miniaturized, and the display has been enlarged. Therefore, the foam sheet has also been reduced in thickness and width. As a result, it is required that even a thin and narrow resin foam sheet have high impact-absorbing properties and impact resistance. In order to improve the impact-absorbing properties and impact resistance of a resin foam material, it is expected, for example, to improve flexibility by increasing the expansion ratio and to increase rigidity by increasing the degree of crosslinking. However, a thin and narrow foam sheet cannot obtain sufficient impact-absorbing properties and impact resistance by simply adjusting the expansion ratio and the degree of crosslinking, and further improvement is desired.

Further, since a touch-sensitive display device is often used in the electronic equipment described above, defects are liable to be generated by the influence of static electricity; for example, the display device will not light up. Therefore, it is also required that a foam sheet have withstand voltage properties.

The present invention has been made in view of the above conventional circumstances, and an object of the present invention is to provide a thin polyolefin resin foam sheet which is excellent in impact-absorbing properties and impact resistance and has withstand voltage properties, and an adhesive tape using the same.

Solution to Problem

As a result of extensive and intensive studies, the present inventors have found that the impact-absorbing properties, impact resistance, and withstand voltage properties of a foam sheet can be improved by blending at least two polyolefin resins having different densities and using the resulting blend as a resin component, and have completed the present invention.

Specifically, the following [1] and [2] are the gist of the present invention.

[1] A polyolefin resin foam sheet having a plurality of cells which is formed by foaming a polyolefin resin composition, wherein the polyolefin resin composition contains a polyolefin resin (A) having relatively high density and a polyolefin resin (B) having relatively low density, and the weighted average resin density of the polyolefin resin (A) and the polyolefin resin (B) is 0.900 g/cm$^3$ or less; and wherein, in the polyolefin resin foam sheet, a ratio of strength at break in the TD direction to the maximum cell size in the MD direction, [TD strength at break/MD maximum cell size], and a ratio of strength at break in the MD direction to the maximum cell size in the TD direction, [MD strength at break/TD maximum cell size], are both 45 kPa/μm or more.

[2] An adhesive tape having a pressure sensitive adhesive layer provided on at least one surface of the polyolefin resin foam sheet according to the above [1].

Advantageous Effects of Invention

The present invention can provide a thin polyolefin resin foam sheet which is excellent in impact-absorbing properties and impact resistance and has withstand voltage properties, and an adhesive tape using the same.

DESCRIPTION OF EMBODIMENTS

[Polyolefin Resin Foam Sheet]

The polyolefin resin foam sheet of the present invention is a polyolefin resin foam sheet having a plurality of cells which is formed by foaming a polyolefin resin composition, wherein the polyolefin resin composition contains a polyolefin resin (A) having relatively high density and a polyolefin resin (B) having relatively low density, and the weighted average resin density of the polyolefin resin (A) and the polyolefin resin (B) is 0.900 g/cm$^3$ or less; and wherein, in the polyolefin resin foam sheet, a ratio of strength at break in the TD direction to the maximum cell size in the MD direction, [TD strength at break/MD maximum cell size], and a ratio of strength at break in the MD direction to the maximum cell size in the TD direction, [MD strength at break/TD maximum cell size], are both 45 kPa/μm or more.

Note that, in the present invention, "MD" means Machine Direction, and it means a direction that is in agreement with the direction of extrusion or the like of a polyolefin resin foam sheet. Further, "TD" means Transverse Direction, and it means a direction that is orthogonal to MD and parallel to the foam sheet.

<Polyolefin Resin Composition>

As the polyolefin resin foam sheet of the present invention, there is used a polyolefin resin composition containing a polyolefin resin (A) having relatively high density and a polyolefin resin (B) having relatively low density, wherein the weighted average resin density of the polyolefin resin (A) and the polyolefin resin (B) is 0.900 g/cm$^3$ or less.

The polyolefin resin (A) is preferably one or more selected from the group consisting of polyolefin resins having a density of 0.900 g/cm$^3$ or more. When the density of the polyolefin resin (A) is equal to or more than the above lower limit, various mechanical strengths, such as interlaminar strength, of the resulting foam sheet will be improved. From such a point of view, the density of the polyolefin resin (A) is more preferably 0.900 to 0.930 g/cm$^3$, further preferably 0.900 to 0.915 g/cm$^3$.

The polyolefin resin (B) is preferably one or more selected from the group consisting of polyolefin resins having a lower density than that of the polyolefin resin (A), for example, having a density of less than 0.900 g/cm$^3$. When the density of the polyolefin resin (B) is less than the above upper limit, the flexibility of the resulting foam sheet will be improved, thereby improving the impact-absorbing properties and impact resistance of the foam sheet even if it is thin and narrow. From such a point of view, the density of the polyolefin resin (B) is more preferably less than 0.890 g/cm$^3$, further preferably 0.865 to 0.885 g/cm$^3$.

Since a mixture of these two polyolefin resins each having a different density is used for the polyolefin resin foam sheet of the present invention, various mechanical strengths, such as interlaminar strength, and flexibility of the foam sheet are improved, and the impact-absorbing properties and impact resistance of the foam sheet are improved even if it is thin and narrow.

In the present invention, the weighted average resin density of the polyolefin resin (A) and the polyolefin resin (B) is 0.900 g/cm$^3$ or less. In the present invention, if the weighted average resin density is larger than 0.900 g/cm$^3$, mechanical strength, flexibility, and the like may not be sufficiently improved even if a mixture of a polyolefin resin (A) and a polyolefin resin (B) having different densities from each other is used. In view of improving the mechanical strength and flexibility, the weighted average resin density is preferably 0.870 to 0.900 g/cm$^3$, more preferably 0.880 to 0.898 g/cm$^3$.

Note that, the weighted average resin density in the present specification refers to a weighted average resin density of the polyolefin resin (A) and the polyolefin resin (B) using the amount (parts by mass) of these resins contained in the polyolefin resin composition as weights.

The polyolefin resin (A) preferably has a higher melting point than the polyolefin resin (B) in view of improving the heat stability of the polyolefin resin composition, preventing the stickiness and blocking during the production of the foam sheet, and improving the processability. Specifically, the melting point of the polyolefin resin (A) is preferably 80° C. or more, more preferably 90 to 120° C.

On the other hand, the melting point of the polyolefin resin (B) is preferably less than 80° C., more preferably 40 to 70° C.

Note that, in the present specification, the melting point of the polyolefin resin (A) and polyolefin resin (B) is measured by a differential scanning calorimetry (DSC) method.

Any one of the polyolefin resin (A) and the polyolefin resin (B) is preferably a polyethylene resin, and both the polyolefin resin (A) and the polyolefin resin (B) are more preferably a polyethylene resin.

As the polyethylene resin, preferred are polyethylene resins polymerized with a polymerization catalyst such as a metallocene compound, a Ziegler-Natta compound, and a chromium oxide compound, and a polyethylene resin polymerized with a metallocene polymerization catalyst is preferred.

When both the polyolefin resin (A) and the polyolefin resin (B) are obtained by using a metallocene polymerization catalyst, various mechanical strengths will be improved, allowing the thickness of a polyolefin resin foam sheet to be reduced while keeping various performances of the foam sheet at a high level.

As a polyethylene resin used as the polyolefin resin (A) and the polyolefin resin (B), preferred is a linear low density polyethylene obtained by copolymerizing ethylene and a small amount of α-olefin as needed.

Here, specific examples of α-olefin include propylene, 1-butene, 1-pentene, 4-methyl-1-pentene, 1-hexene, 1-heptene, and 1-octene. Among them, α-olefin having 4 to 10 carbon atoms is preferred, and 1-hexene and 1-octene are particularly preferred.

However, a polyethylene resin used as the polyolefin resin (A) may be a low density polyethylene (LDPE) produced with a radical polymerization catalyst under high pressure or may be a combination of LDPE and the linear low density polyethylene described above.

The polyolefin resin (A) and the polyolefin resin (B) are preferably different from each other in crystallinity, and thereby the resins are preferably different from each other in the density and the melting point. For example, even when both the polyolefin resin (A) and the polyolefin resin (B) are composed of a linear low density polyethylene and the same α-olefin as a comonomer, the polyolefin resin (A) and the polyolefin resin (B) will be different from each other in the density and the melting point if the resins are different from each other in crystallinity.

In the present invention, the mass ratio of the polyolefin resin (A) to the polyolefin resin (B), [(A)/(B)], is preferably 0.20 to 10. When the mass ratio is within the above range, the flexibility of the polyolefin resin foam sheet will be satisfactorily maintained, and at the same time, various mechanical strengths thereof can be improved to improve impact resistance and impact-absorbing properties. From such a point of view, the mass ratio [(A)/(B)] is preferably 0.20 or more, more preferably 0.60 or more, further preferably 1.0 or more, further more preferably 1.4 or more, further more preferably 1.8 or more, and further more preferably 2.0 or more; and preferably 10 or less, more preferably 8.0 or less, further preferably 6.0 or less, further more preferably 4.0 or less, further more preferably 3.2 or less, and further more preferably 2.8 or less; and specifically, more preferably 0.60 to 8.0, further preferably 0.60 to 7.0, further more preferably 1.0 to 6.0, further more preferably 1.0 to 4.0, further more preferably 1.4 to 4.0, further more preferably 1.8 to 3.2, and further more preferably 2.0 to 2.8. When the mass ratio is equal to or more than the above lower limits, various mechanical strengths such as tensile strength, tear strength, and interlaminar strength of the polyolefin resin foam sheet will be improved, and at the same time, the stickiness, blocking, and the like during processing are prevented, improving the processability of the foam sheet. Further, when the mass ratio is equal to or less than the above upper limits, physical properties such as flexibility of the polyolefin resin foam sheet will be improved to improve the impact resistance and the impact-absorbing properties.

[Metallocene Compound]

Examples of the metallocene compounds suitable in the present invention include a compound such as a bis(cyclopentadienyl) metal complex having a structure in which a transition metal is sandwiched by unsaturated compounds each having a π-electron system. More specific examples include a compound in which one or more cyclopentadienyl rings or analogs thereof are present as ligands on a tetravalent transition metal such as titanium, zirconium, nickel, palladium, hafnium, and platinum.

In such a metallocene compound, active sites have uniform properties, and each active site has the same degree of activity. A polymer synthesized using a metallocene compound has high uniformity in molecular weight, molecular weight distribution, composition, composition distribution, and the like. Therefore, when a sheet containing a polymer synthesized using a metallocene compound is crosslinked, the crosslinking proceeds uniformly. Since a uniformly crosslinked sheet can be uniformly stretched, the resulting polyolefin resin foam sheet can have a uniform thickness.

Examples of the ligands include a cyclopentadienyl ring and an indenyl ring. These cyclic compounds may be substituted with a hydrocarbon group, a substituted hydrocarbon group, or a hydrocarbon-substituted metalloid group. Examples of the hydrocarbon group include a methyl group, an ethyl group, various propyl groups, various butyl groups, various amyl groups, various hexyl groups, a 2-ethylhexyl group, various heptyl groups, various octyl groups, various nonyl groups, various decyl groups, various cetyl groups, and a phenyl group. Note that "various" means various isomers including n-, sec-, tert-, and iso-.

Further, an oligomer obtained by polymerizing a cyclic compound may be used as a ligand.

Furthermore, a monovalent anion ligand such as chloride and bromide, a bivalent anion chelate ligand, hydrocarbon, alkoxide, arylamide, aryloxide, amide, arylamide, phosphide, arylphosphide, and the like may be used in addition to the unsaturated compounds each having a π-electron system.

Examples of the metallocene compound containing a tetravalent transition metal and a ligand include cyclopentadienyltitanium tris(dimethylamide), methylcyclopentadienyltitanium tris(dimethylamide), bis(cyclopentadienyl)titanium dichloride, and dimethylsilyltetramethylcyclopentadienyl-t-butylamidezirconium dichloride.

A metallocene compound exhibits the action as a catalyst by using it in combination with a specific cocatalyst (promoter) when various olefins are polymerized. Specific examples of the cocatalyst include methyl aluminoxane (MAO) and a boron-based compound. Note that the ratio of the molar amount of the cocatalyst to be used relative to that of the metallocene compound is preferably 10 to 1,000,000, more preferably 50 to 5,000.

[Ziegler-Natta Compound]

The Ziegler-Natta compound is a triethylaluminum-titanium tetrachloride solid composite, and is preferably produced by a method including producing a titanium trichloride composition by reducing titanium tetrachloride with an organoaluminum compound and treating with various electron donors and electron acceptors, and then combining the titanium trichloride composition, an organoaluminum compound, and an aromatic carboxylate (refer to JP 56-100806 A, JP 56-120712 A, and JP 58-104907 A), a method involving using a supported catalyst in which titanium tetrachloride and various electron donors are brought into contact with a magnesium halide (refer to JP 57-63310 A, JP 63-43915 A, and JP 63-83116 A), or the like.

<Other Polyolefin Resins>

The polyolefin resin composition used in the present invention may contain other polyolefin resins in addition to the polyolefin resin (A) and the polyolefin resin (B).

Examples of other polyolefin resins include other polyethylene resins such as an ethylene-vinylacetate copolymer containing 50% by mass or more of ethylene and a polypropylene resin. These may be used singly or in combination of two or more. Examples of the polypropylene resin include a propylene homopolymer and a propylene-α-olefin copolymer containing 50% by mass or more of propylene. These may be used singly or in combination of two or more.

Specific examples of α-olefins constituting the propylene-α-olefin copolymer include ethylene, 1-butene, 1-pentene, 4-methyl-1-pentene, 1-hexene, 1-heptene, and 1-octene, and α-olefins having 6 to 12 carbon atoms are preferred among them.

The polyolefin resin composition used in the present invention may contain the above other resins as long as the performance of a polyolefin resin foam sheet is not impaired, but it is preferred that the resin composition do not contain other resins. When the polyolefin resin composition contains other resins, the content thereof is preferably 30% by mass or less, more preferably 10% by mass or less, further preferably 5% by mass or less, in the polyolefin resin composition.

Examples of commercially available products of the polyolefin resin (A) include "Kernel KF370" (density: 0.905 g/cm$^3$, melting point Tm by a DSC method: 97° C.) manufactured by Japan Polyethylene Corporation, which is an ethylene-1-hexene copolymer produced using a metallocene polymerization catalyst, and "Suntec-LD L2340" (density: 0.923 g/cm$^3$, melting point Tm by a DSC method: 112° C.) manufactured by Asahi Kasei Chemicals Corporation, which is a low density polyethylene (LDPE) produced with a radical polymerization catalyst under high pressure.

Examples of commercially available products of the polyolefin resin (B) include "Affinity EG8200" (density: 0.870 g/cm$^3$, melting point Tm by a DSC method: 63° C.) manufactured by The Dow Chemical Company, "Affinity KC8852" (density: 0.875 g/cm$^3$, melting point Tm by a DSC method: 66° C.) manufactured by The Dow Chemical Company, "Affinity PF1140G" (density: 0.897 g/cm$^3$, melting point Tm by a DSC method: 96° C.) manufactured by The Dow Chemical Company, and "Affinity PF8770G1" (density: 0.885 g/cm$^3$, melting point Tm by a DSC method: 82° C.) manufactured by The Dow Chemical Company, which are ethylene-1-octene copolymers produced using a metallocene polymerization catalyst.

Further examples include "Kernel KF650T" (density: 0.888 g/cm$^3$, melting point Tm by a DSC method: 55° C.) manufactured by Japan Polyethylene Corporation, "Kernel KS240T" (density: 0.880 g/cm$^3$, melting point (DSC method) Tm: 60° C., MFR: 2.2) manufactured by Japan Polyethylene Corporation, and "Kernel KS340T" (density: 0.880 g/cm$^3$, melting point Tm by a DSC method: 60° C., MFR: 3.5) manufactured by Japan Polyethylene Corporation, which are ethylene-1-hexene copolymers produced using a metallocene polymerization catalyst.

<Ratio of Strength at Break to Average Cell Size>

In the polyolefin resin foam sheet of the present invention, a ratio of strength at break in the TD direction to the average cell size in the MD direction, [TD strength at break/MD average cell size], and a ratio of strength at break in the MD direction to the average cell size in the TD direction, [MD strength at break/TD average cell size], are both 80 kPa/μm or more, preferably 85 kPa/μm or more, more preferably 90 kPa/μm or more, further preferably 100 kPa/μm or more, further more preferably 110 kPa/μm or more, further more preferably 120 kPa/μm or more, and further more preferably 130 kPa/μm or more; and preferably 500 kPa/μm or less, more preferably 450 kPa/μm or less, further preferably 400 kPa/μm or less, further more preferably 350 kPa/μm or less, and further more preferably 300 kPa/μm or less; and specifically, preferably 85 to 500 kPa/μm, more preferably 90 to 500 kPa/μm, further preferably 90 to 450 kPa/μm, and further more preferably 90 to 400 kPa/μm. When the ratio is within the above ranges, there will be obtained a polyolefin resin foam sheet which is excellent in the balance between the withstand voltage properties in the MD direction and those in the TD direction.

In the present invention, the average value of the ratio [TD strength at break/MD average cell size] and the ratio [MD strength at break/TD average cell size] is preferably 90 kPa/μm or more, more preferably 95 kPa/μm or more, further preferably 100 kPa/μm or more, further more preferably 110 kPa/μm or more, further more preferably 120 kPa/μm or more, further more preferably 130 kPa/μm or more, further more preferably 140 kPa/μm or more, and further more preferably 150 kPa/μm or more; and preferably 500 kPa/μm or less, more preferably 450 kPa/μm or less, further preferably 400 kPa/μm or less, further more preferably 350 kPa/μm or less, further more preferably 300 kPa/μm or less, and further more preferably 250 kPa/μm or less; specifically, more preferably 95 to 500 kPa/μm, further preferably 100 to 500 kPa/μm, further more preferably 100 to 450 kPa/μm, and further more preferably 100 to 400 kPa/μm. When the average value of the ratio is within the above ranges, there will be obtained a polyolefin resin foam sheet which is excellent in impact-absorbing properties and impact resistance.

<Average Cell Sizes in MD Direction and TD Direction>

The average cell size in the MD direction of the polyolefin resin foam sheet of the present invention is preferably 50 μm or more, more preferably 60 μm or more; and preferably 200 μm or less, more preferably 150 μm or less, further preferably 120 μm or less, and further more preferably 110 μm or less; specifically, preferably 50 to 200 μm, more preferably 50 to 150 μm, and further preferably 50 to 120 μm.

Further, the average cell size in the TD direction of the polyolefin resin foam sheet of the present invention is preferably 50 μm or more, more preferably 60 μm or more; and preferably 200 μm or less, more preferably 150 μm or less, further preferably 120 μm or less, further more preferably 100 μm or less, and further more preferably 90 μm or less; specifically, preferably 50 to 200 μm, more preferably 50 to 150 μm, and further preferably 50 to 100 μm.

When the average cell sizes in the MD direction and the TD direction of the polyolefin resin foam sheet are within the above ranges, the impact-absorbing properties, impact resistance, and withstand voltage properties will be improved. Note that the average cell size is measured in accordance with the method in Examples to be described below.

<Ratio of Strength at Break to Maximum Cell Size>

In the polyolefin resin foam sheet of the present invention, a ratio of strength at break in the TD direction to the maximum cell size in the MD direction, [TD strength at break/MD maximum cell size], and a ratio of strength at break in the MD direction to the maximum cell size in the TD direction, [MD strength at break/TD maximum cell size], are both 45 kPa/μm or more, preferably 50 kPa/μm or more, and more preferably 55 kPa/μm or more; and preferably 250 kPa/μm or less, more preferably 200 kPa/μm or less, further preferably 150 kPa/μm or less, further more preferably 120 kPa/μm or less, further more preferably 110 kPa/μm or less, further more preferably 100 kPa/μm or less, and further more preferably 95 kPa/μm or less; specifically, preferably 50 to 250 kPa/μm, more preferably 55 to 250 kPa/μm, and further preferably 55 to 200 kPa/μm. When the ratio is within the above ranges, there will be obtained a polyolefin resin foam sheet which is excellent in the balance between the withstand voltage properties in the MD direction and those in the TD direction.

In the present invention, the average value of the ratio [TD strength at break/MD maximum cell size] and the ratio [MD strength at break/TD maximum cell size] is preferably 50 kPa/μm or more, more preferably 55 kPa/μm or more, and further preferably 60 kPa/μm or more; and preferably 250 kPa/μm or less, more preferably 200 kPa/μm or less, further preferably 150 kPa/μm or less, further more preferably 120 kPa/μm or less, further more preferably 110 kPa/μm or less, further more preferably 100 kPa/μm or less, and further more preferably 90 kPa/μm or less; specifically, more preferably 55 to 250 kPa/μm, further preferably 60 to 250 kPa/μm, and further more preferably 60 to 200 kPa/μm. When the average value of the ratio is within the above ranges, there will be obtained a polyolefin resin foam sheet which is excellent in impact-absorbing properties and impact resistance.

<Maximum Cell Sizes in MD Direction and TD Direction>

The maximum cell size in the MD direction of the polyolefin resin foam sheet of the present invention is preferably 100 μm or more, more preferably 130 μm or more, and further preferably 160 μm or more; and preferably 300 μm or less, more preferably 270 μm or less, and further preferably 230 μm or less; specifically, preferably 100 to 300 μm, more preferably 100 to 270 μm, and further preferably 100 to 230 μm.

Further, the maximum cell size in the TD direction of the polyolefin resin foam sheet of the present invention is preferably 100 μm or more, more preferably 130 μm or more, and further preferably 160 μm or more; and preferably 300 μm or less, more preferably 270 μm or less, and further preferably 240 μm or less; and preferably 100 to 300 μm, more preferably 100 to 270 μm, and further preferably 100 to 240 μm.

When the maximum cell sizes in the MD direction and the TD direction of the polyolefin resin foam sheet are within the above ranges, the impact-absorbing properties, impact resistance, and withstand voltage properties will be improved. Note that the maximum cell size is measured in accordance with the method in Examples to be described below.

<Thickness>

The thickness of the polyolefin resin foam sheet of the present invention is preferably 0.02 to 1.9 mm, more preferably 0.03 to 1.0 mm, and further preferably 0.04 to 0.5 mm. When the thickness is equal to or more than the above lower limits, high mechanical strength can be secured, and excellent impact resistance and impact-absorbing properties will be easily obtained. Further, when the thickness is equal to or less than the above upper limits, the polyolefin resin foam sheet will be easily used in miniaturized electronic equipment.

<Density>

In the present invention, the density of the polyolefin resin foam sheet is preferably 0.30 g/cm$^3$ or more, more preferably 0.35 g/cm$^3$ or more; and preferably 0.85 g/cm$^3$ or less, more preferably 0.80 g/cm$^3$ or less; specifically, preferably 0.30 to 0.85 g/cm$^3$, more preferably 0.35 to 0.80 g/cm$^3$. When the density is equal to or more than the above lower limits, the impact resistance of the resin foam sheet will be improved. Further, when the density is equal to or less than the above upper limits, flexibility will be improved.

<Degree of Crosslinking (Gel Fraction)>

The polyolefin resin foam sheet of the present invention is preferably crosslinked in view of improving impact resistance and impact-absorbing properties. When the sheet is crosslinked, the degree of crosslinking (gel fraction) is preferably 2 to 70% by mass, more preferably 10 to 65% by mass, and further preferably 15 to 60% by mass. When the degree of crosslinking is equal to or more than the above lower limits, sufficient crosslinking will be formed in the polyolefin resin foam sheet, thus capable of improving both impact-absorbing properties and impact resistance. Further, when the degree of crosslinking is equal to or less than the above upper limits, the flexibility of the polyolefin resin foam sheet will be secured, thus capable of obtaining suitable impact-absorbing properties. Note that the degree of crosslinking can be represented by the gel fraction measured by the measuring method to be described below.

<25% Compressive Strength>

The 25% compressive strength of the polyolefin resin foam sheet is, but not limited to, preferably 100 kPa or more, more preferably 150 kPa or more, further preferably 200 kPa or more, further more preferably 250 kPa or more, and further more preferably 300 kPa or more; and preferably 2,000 kPa or less, more preferably 1,800 kPa or less, further preferably 1,600 kPa or less, further more preferably 1,400 kPa or less, further more preferably 1,200 kPa or less, and further more preferably 1,000 kPa or less; specifically, preferably 100 to 2,000 kPa, more preferably 150 to 1,800 kPa. When the 25% compressive strength is equal to or less than the above upper limits, the flexibility of the polyolefin resin foam sheet will be improved, and when the foam sheet is used for forming a tape, the followability to an adherend will be improved. This is advantageous in that neither water nor air can easily enter the inner part of electronic equipment. Further, when the 25% compressive strength is equal to or more than the above lower limits, both impact-absorbing properties and impact resistance will be improved. Note that the 25% compressive strength is obtained by measuring the polyolefin resin foam sheet according to JIS K6767.

<Interlaminar Strength>

The interlaminar strength of the foam sheet is preferably 2,000 to 10,000 kPa, more preferably 2,500 to 9,500 kPa, and further preferably 3,000 to 9,000 kPa. When an impact is given to such a thin foam sheet as in the present invention, a large stress will act in the thickness direction by the impact force. Therefore, when the interlaminar strength is set to the above lower limits or more, the strength against stress will be increased to improve the impact resistance of the foam sheet. Further, when the interlaminar strength is set to the above upper limits or less, the flexibility of the foam sheet will be maintained, thus capable of easily obtaining a foam sheet having high impact-absorbing properties and high sealing properties.

Note that in the present specification, the interlaminar strength refers to a value showing the tensile strength in the thickness direction, and it can be measured by the method described in Examples to be described below.

<Closed Cell>

The polyolefin resin foam sheet of the present invention has a large number of cells, and the cells are preferably closed cells. Note that in the present specification, "the cells being closed cells" means that the proportion of closed cells relative to all the cells (referred to as "percentage of closed cells") is 70% or more.

The percentage of closed cells is determined according to JIS K7138 (2006) or ASTM D2856 (1998). Examples of commercially available measuring devices include an Air Comparison Pycnometer "MODEL 930" manufactured by Beckman Instruments, Inc. and a dry automatic density meter AccuPyc 1330.

The percentage of closed cells is measured, for example, in the following manner. A test piece having a planar square shape having a side of 5 cm and having a certain thickness is cut from a polyolefin resin foam sheet. The thickness of the test piece is measured to calculate the apparent volume $V_1$ of the test piece, and the weight $W_1$ of the test piece is measured. Next, the apparent volume $V_2$ of the cells is calculated based on the following formula. Note that the density of the resin constituting the test piece is defined as 1 g/cm$^3$.

Apparent volume $V_2$ of cells=$V_1-W_1$

Subsequently, the test piece is sunk in distilled water at 23° C. to a depth of 100 mm from the water surface, and a pressure of 15 kPa is applied to the test piece over 3 minutes. After releasing the pressure in the water, the test piece is taken out of the water; the water adhered to the surfaces of the test piece is removed; the weight $W_2$ of the test piece is measured; and the percentage of open cells $F_1$ and the percentage of closed cells $F_2$ are calculated based on the following formulas.

Percentage of open cells $F_1(\%)=100\times(W_2-W_1)/V_2$

Percentage of closed cells $F_2(\%)=100-F_1$

[Method for Producing Polyolefin Resin Foam Sheet]

The polyolefin resin foam sheet of the present invention can be produced by foaming a polyolefin resin composition by a common method. The method for producing the polyolefin resin foam sheet is not limited, and the foam sheet can also be produced by crosslinking the polyolefin resin composition as needed followed by foaming.

When the polyolefin resin foam sheet of the present invention is produced as a crosslinked polyolefin resin foam sheet, it is industrially advantageous to produce the crosslinked sheet, for example, by a production method comprising the following steps (1) to (3):

Step (1): A step of obtaining a sheet-shaped polyolefin resin composition by feeding a polyolefin resin (A), a polyolefin resin (B), a blowing agent of heat decomposition type, and other additives to an extruder, melt-kneading these components, and extruding the melt-kneaded mixture from the extruder into a sheet shape;

Step (2): A step of crosslinking the sheet-shaped polyolefin resin composition; and Step (3): A step of heating the sheet-shaped crosslinked polyolefin resin composition to foam the blowing agent of heat decomposition type and stretching the sheet preferably either in the MD direction or in the TD direction, or in both directions.

Note that, instead of the method described above, the crosslinked polyolefin resin foam sheet can also be produced by a method described in WO 2005/007731.

Examples of the blowing agent of heat decomposition type include, but are not particularly limited to, azodicarbonamide, N,N'-dinitrosopentamethylenetetramine, and p-toluenesulfonyl semicarbazide.

Among them, azodicarbonamide is preferred. Note that the blowing agents of heat decomposition type may be used singly or in combination of two or more.

The content of the blowing agent of heat decomposition type in the polyolefin resin composition is preferably 1 to 12 parts by mass, more preferably 1 to 8 parts by mass, based on 100 parts by mass of a polyolefin resin. When the content of the blowing agent of heat decomposition type is within the above ranges, the foamability of the polyolefin resin composition will be improved; a crosslinked polyolefin resin foam sheet having a desired expansion ratio will be easily obtained; and impact resistance and impact-absorbing properties will be improved.

Examples of other additives used in the step (1) include a decomposition temperature regulator, a crosslinking auxiliary, and an antioxidant.

The decomposition temperature regulator is blended for reducing the decomposition temperature of the blowing agent of heat decomposition type or increasing or controlling the decomposition rate, and examples of specific compounds thereof include zinc oxide, zinc stearate, and urea. The decomposition temperature regulator is blended, for example, in an amount of 0.01 to 5 parts by mass based on 100 parts by mass of the polyolefin resin, in order to adjust the surface state or the like of the foam sheet.

A polyfunctional monomer can be used as a crosslinking auxiliary. Addition of the crosslinking auxiliary to the polyolefin resin reduces the dose of ionizing radiation radiated in step (2) to be described below to thereby prevent the cutting and degradation of resin molecules accompanying the irradiation with the ionizing radiation.

Specific examples of the crosslinking auxiliary include compounds having three functional groups in one molecule, such as trimethylolpropane trimethacrylate, trimethylolpropane triacrylate, triallyl trimellitate ester, triallyl 1,2,4-benzenetricarboxylate ester, and triallyl isocyanurate; compounds having two functional groups in one molecule, such as 1,6-hexanediol dimethacrylate, 1,9-nonanediol dimethacrylate, 1,10-decanediol dimethacrylate, and divinylbenzene; diallyl phthalate, diallyl terephthalate, diallyl isophthalate, ethylvinylbenzene, neopentyl glycol dimethacrylate, lauryl methacrylate, and stearyl methacrylate. These crosslinking auxiliaries are used singly or in combination of two or more.

The amount of the crosslinking auxiliary added is preferably 0.2 to 10 parts by mass, more preferably 0.3 to 5 parts by mass, further preferably 0.5 to 5 parts by mass, based on 100 parts by mass of the resin components. When the amount of the crosslinking auxiliary added is 0.2 parts by mass or more, the foam sheet can stably obtain a desired degree of crosslinking, and when the amount of the crosslinking auxiliary added is 10 parts by mass or less, the control of the degree of crosslinking of the foam sheet will be easy.

Further, examples of the antioxidant include phenolic antioxidants, such as 2,6-di-t-butyl-p-cresol.

Examples of the methods of foaming the polyolefin resin composition include, but are not particularly limited to, a method including heating the polyolefin resin composition with hot air, a method including heating it with infrared rays, a method including heating it with a salt bath, and a method including heating it with an oil bath. These methods may be used in combination.

Note that the foaming of the polyolefin resin composition is not limited to the case of using a blowing agent of heat decomposition type, and physical expansion with butane gas or the like may be used.

Examples of the method for crosslinking the polyolefin resin composition include a method including irradiating the polyolefin resin composition with ionizing radiation, such as electron beams, $\alpha$-rays, $\beta$-rays, and $\gamma$-rays, and a method including blending an organic peroxide with the polyolefin resin composition in advance and heating the polyolefin resin composition to decompose the organic peroxide. These methods may be used in combination. Among them, the method including irradiating the resin composition with ionizing radiation is preferred.

The dose of ionizing radiation is preferably 0.50 to 10 Mrad, more preferably 2.5 to 8.0 Mrad so that the gel fraction may be 2 to 70% by mass.

Examples of the organic peroxide used for crosslinking include 1,1-bis(t-butylperoxy)3,3,5-trimethylcyclohexane and 1,1-bis(t-butylperoxy)cyclohexane. These may be used singly or in combination of two or more. The amount of the organic peroxide added is preferably 0.01 to 5 parts by mass, more preferably 0.1 to 3 parts by mass, based on 100 parts by mass of the polyolefin resin. When the amount of the organic peroxide added is within the above ranges, the crosslinking of the polyolefin resin composition will easily proceed, and the amount of the decomposed residue of the organic peroxide in the resulting crosslinked polyolefin resin foam sheet will be suppressed.

The polyolefin resin foam sheet of the present invention is preferably stretched, as described above. The stretching may be performed after the polyolefin resin composition is foamed to obtain a foam sheet, or may be performed while foaming the polyolefin resin composition. Note that when a foam sheet is stretched after the polyolefin resin composition is foamed to obtain a foam sheet, the foam sheet is preferably stretched without break while maintaining the molten state during the foaming without cooling the foam sheet, but a foam sheet may also be stretched after the foam sheet is cooled and then heated again to a melted or a softened state.

Further, the stretching ratio in the MD direction of the polyolefin resin foam sheet is preferably 1.1 to 3.0, more preferably 1.3 to 2.8. When the stretching ratio in the MD direction of the polyolefin resin foam sheet is set to the above lower limits or more, the flexibility and tensile strength of the polyolefin resin foam sheet will be easily improved. On the other hand, when the stretching ratio in the MD direction of the polyolefin resin foam sheet is set to the above upper limits or less, the foam sheet will be prevented from breaking during stretching; the reduction of expansion ratio by the escape of blowing gas from the foam sheet during foaming will be prevented; the flexibility and tensile strength of the polyolefin resin foam sheet will be improved; and the quality will also be easily uniform. Further, the polyolefin resin foam sheet may also be stretched in the TD direction at a stretching ratio within the above ranges.

[Adhesive Tape]

The adhesive tape of the present invention comprises a polyolefin resin foam sheet according to the present invention as a base material and a pressure sensitive adhesive layer provided on at least one surface or both surfaces of the polyolefin resin foam sheet. The adhesive tape has a thickness of generally 0.03 to 2.0 mm, preferably 0.03 to 1.0 mm.

The pressure sensitive adhesive layer constituting the adhesive tape preferably has a thickness of 5 to 200 µm, more preferably 7 to 150 µm, further preferably 10 to 100 µm. When the pressure sensitive adhesive layer constituting the adhesive tape has a thickness in the range of 5 to 200 µm, the adhesive tape and electronic equipment using the adhesive tape will be reduced in thickness.

Examples of the pressure sensitive adhesive constituting the pressure sensitive adhesive layer laminated on at least one surface or both surfaces of the polyolefin resin foam sheet include, but are not particularly limited to, an acrylic pressure sensitive adhesive, a urethane pressure sensitive adhesive, a rubber pressure sensitive adhesive, and a silicone pressure sensitive adhesive.

Examples of the method of applying a pressure sensitive adhesive to at least one surface of a polyolefin resin foam sheet so as to laminate a pressure sensitive adhesive layer to the foam sheet include a method including applying a pressure sensitive adhesive to at least one surface of a polyolefin resin foam sheet using a coating machine such as a coater, a method including spraying/applying a pressure sensitive adhesive to at least one surface of a polyolefin resin foam sheet using a sprayer, and a method including applying a pressure sensitive adhesive to at least one surface of a polyolefin resin foam sheet using a brush.

[Method of Using Polyolefin Resin Foam Sheet]

The polyolefin resin foam sheet and the adhesive tape are used, for example, in the body of electronic equipment such as a mobile phone and a video camera, and are more preferably used for the display device of a mobile phone.

Each of foam sheet and the adhesive tape is used, for example, in the state where it is sandwiched between two members and compressed in the thickness direction. Thus, the foam sheet and the adhesive tape are each used as an impact absorber which absorbs the impact acting on any one or both of the members or as a sealing material which prevents dust and the like from entering between the two members.

EXAMPLES

The present invention will be described further in detail with Examples, but the present invention is not limited at all by these Examples.

[Measuring Methods]

The measuring method of each physical property in the present specification is as follows.

<Weighted Average Resin Density>

The weighted average resin density of the polyolefin resin (A) and the polyolefin resin (B) was obtained by calculating a weighted average of the density of a polyolefin resin constituting the polyolefin resin (A) and the density of a polyolefin resin constituting the polyolefin resin (B) using the amount in parts by mass of each polyolefin resin as weights.

Note that the density of each polyolefin resin was measured according to ASTM D792.

<Density and Expansion ratio of Polyolefin Resin Foam Sheet>

The density of the polyolefin resin foam sheet was measured according to JIS K7222. Note that the expansion ratio is a reciprocal of the density.

<Degree of Crosslinking (% by mass)>

A test piece weighing about 50 mg is taken from a crosslinked polyolefin resin foam sheet and precisely weighed to obtain the weight A (mg) of the test piece. Next, the test piece is immersed in 30 cm$^3$ of xylene at 105° C., allowed to stand for 24 hours, and then filtered through a 200-mesh wire net to collect insoluble matter on the wire net. The insoluble matter is vacuum dried and precisely weighed to obtain the weight B (mg) of the insoluble matter. From the obtained values, the degree of crosslinking (% by mass) is calculated by the following formula.

Degree of crosslinking (% by mass)=100×(B/A)

<Strengths at Break in MD Direction and TD Direction>

A polyolefin resin foam sheet was cut into a shape of the dumbbell No. 1 specified in JIS K6251 4.1. This was used as a sample and measured for the strengths at break in the MD direction and the TD direction at a measurement temperature of 23° C. according to JIS K6767.

<Average Cell Size and Maximum Cell Size>

A foam sample for measurement was cut to a 50-mm square, immersed in liquid nitrogen for 1 minute, and then cut with a razor along a surface parallel to the MD direction and thickness direction. Subsequently, a photograph at a magnification of 200 was taken using a digital microscope (product name VHX-900, manufactured by Keyence Corporation) and measured for the cell sizes in the MD direction of all the cells present in the cut surface for a length of 2 mm in the MD direction. The operation was repeated 5 times, and the average value of all the cell sizes in the MD direction was defined as the average cell size in the MD direction.

A photograph at a magnification of 200 was taken in the same manner as above except that the foam sample was cut along a surface parallel to the TD direction and the thickness direction, and measured for the cell sizes in the TD direction of all the cells present in the cut surface for a length of 2 mm in the TD direction. The operation was repeated 5 times. Subsequently, the average value of all the cell sizes in the TD direction was defined as the average cell size in the TD direction.

Further, in the measured cell sizes in the MD direction and the TD direction, the largest cell size in the MD direction was defined as the maximum cell size in the MD direction, and the largest cell size in the TD direction was defined as the maximum cell size in the TD direction.

<25% Compressive Strength>

The 25% compressive strength of a polyolefin resin foam sheet was measured according to JIS K 6767.

<Interlaminar Strength>

A primer ("PPX primer" manufactured by Cemedine Co., Ltd.) was applied to a 25-mm square area of a foam sheet, and then an adhesive ("PPX" manufactured by Cemedine Co., Ltd.) was dropped on the center of the application portion in an amount corresponding to a diameter of the drop of 5 mm. Immediately after this, an aluminum jig A of a 25-mm square was placed on the portion where the adhesive was dropped, and the foam sheet and the jig A were adhered by applying pressure. Subsequently, the foam sheet was cut along the size of the jig A. The primer was applied to the surface of the cut foam sheet where the jig A was not adhered, and the adhesive was dropped on the center of the application portion in an amount corresponding to a diameter of the drop of 5 mm. Immediately after this, an aluminum jig B of a 10-mm square was placed on the portion where the adhesive was dropped, and the foam sheet and the jig B were adhered by applying pressure. After the adhesive squeezed out around the jig B was wiped off, the foam sheet was cut along the size of the jig B. The resulting laminate was allowed to stand for 30 minutes at room temperature to cure the adhesive, obtaining a sample for measuring interlaminar strength.

Subsequently, the sample for measuring interlaminar strength was attached to a testing machine ("TENSILON Universal Testing Machine" manufactured by A&D Company, Limited) equipped with a load cell of 1 kN so that the sheet surface of the foam sheet might be perpendicular to the tensile direction. One of the jigs was pulled perpendicularly upward at a rate of 100 mm/min to delaminate only the area of a 1-cm square of the foam sheet. The maximum load at this time was measured, which was used as the first result of the measurement. The same operation was repeated 3 times, and the average value was defined as the interlaminar strength.

Figure 1:
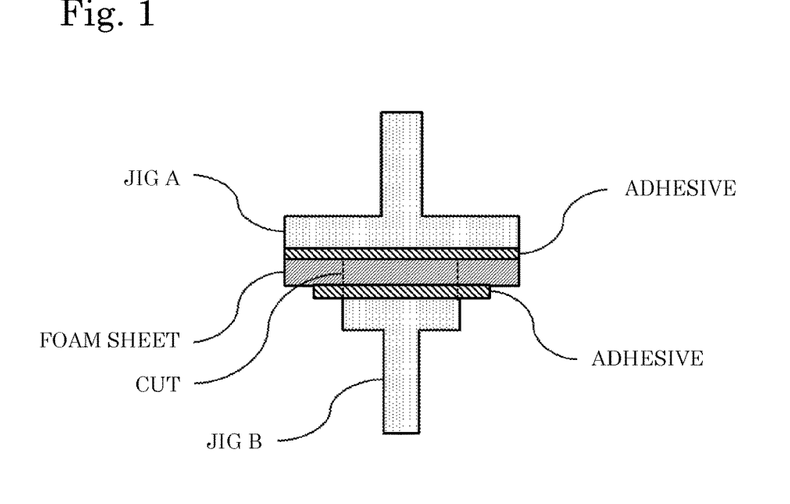
FIG. 1 is a schematic diagram of a testing device for evaluating the interlaminar strength in Examples and Comparative Examples.

Note that a schematic diagram of the testing device used for measuring the interlaminar strength is shown in FIG. 1.

<Withstand Voltage Properties>

A tape-shaped crosslinked polyolefin resin foam sheet having a width of 0.7 mm and a length of 100 mm was sandwiched in the thickness direction between two acrylic sheets and sandwiched in the width direction between two aluminum sheets arranged between the acrylic sheets. A direct-current voltage was applied to the foam sheet in the width direction using "TOS501" (maximum voltage: 12 kV) manufactured by Kikusui Electronics Corporation as a withstand voltage tester under the conditions of 23° C. and 50% RH, and when no current flow was observed for 30 seconds at the voltage, the applied voltage was increased by a 0.5-kV unit. The voltage at which current flows through the foam sheet was measured. Then, the same measurement was performed 3 times, and the average value was defined as the measured value of withstand voltage performance. Note that, in this measurement, a current of 0.1 mA or less was regarded as no current flow, and the measurement was performed for each case where the MD and TD direction of the foam sheet is used as the width direction of the tape-shaped sample.

(Evaluation Criteria)

When the measured values in the MD direction and the TD direction were both 8.0 kV or more, such a foam sheet was rated as "1", noting that the withstand voltage performance was good.

When any one of the measured values in the MD direction and the TD direction was less than 8.0 kV, such a foam sheet was rated as "2", noting that the withstand voltage performance was not good.

<Impact Resistance>

(Preparation of Sample for Impact Resistance Evaluation)

A pressure sensitive adhesive sheet obtained by the following method was laminated on each of both surfaces of the polyolefin resin foam sheets obtained in Examples and Comparative Examples to prepare a double-coated adhesive tape having a polyolefin resin foam sheet as a base material.

(Method for Preparing Pressure Sensitive Adhesive Sheet)

To a reactor equipped with a thermometer, a stirrer, and a cooling tube, were added 75 parts by mass of butyl acrylate, 22 parts by mass of 2-ethylhexyl acrylate, 3 parts by mass of acrylic acid, 0.2 part by mass of 2-hydroxyethyl acrylate, and 80 parts by mass of ethyl acetate. Then, the air in the reactor was replaced with nitrogen, and the reactor was heated to start reflux. Subsequently, 0.1 part by mass of azobisisobutyronitrile was added to the above reactor as a polymerization initiator. The mixture was refluxed for 5 hours to obtain a solution of an acrylic copolymer (z). The resulting acrylic copolymer (z) was measured for the weight average molecular weight by a GPC method using "2690 Separations Model" manufactured by Water Inc. as a column, and the weight average molecular weight was found to be 600,000.

To 100 parts by mass of solids of the acrylic copolymer (z) contained in the resulting solution of the acrylic copolymer (z), were added 15 parts by mass of polymerized rosin ester having a softening point of 135° C., 125 parts by mass of ethyl acetate (manufactured by Fuji Chemicals Ltd.), and 2 parts by mass of an isocyanate crosslinking agent (Coronate L45, manufactured by Tosoh Corp.), followed by stirring the mixture to obtain a pressure sensitive adhesive (Z). Note that the degree of crosslinking of the acrylic pressure sensitive adhesive was 33% by mass.

A release paper having a thickness of 150 μm was provided. The pressure sensitive adhesive (Z) was applied to the release-treated surface of the release paper and dried for 5 minutes at 100° C. to thereby form an acrylic pressure sensitive adhesive layer having a thickness of 50 μm. This acrylic pressure sensitive adhesive layer was bonded together with the surface of a base material composed of a polyolefin foam. Next, in the same manner, the same acrylic pressure sensitive adhesive layer was bonded together also with the opposite surface of the base material composed of a polyolefin foam. Thereby, a pressure sensitive adhesive sheet covered with the release paper having a thickness of 150 μm was obtained.

(Preparation of Impact Resistance Testing Device)

Figure 2:
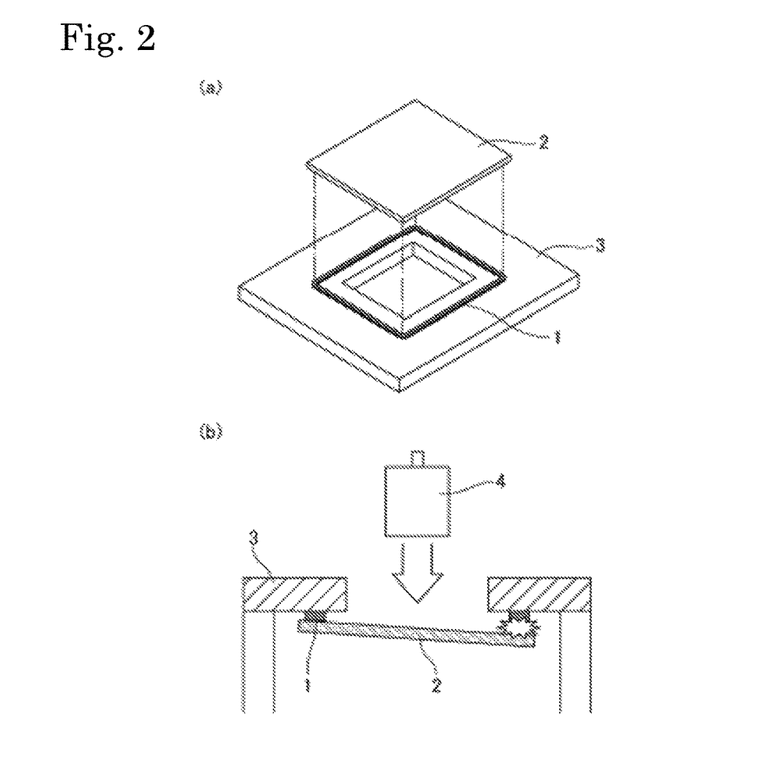
FIG. 2 is a schematic diagram of a testing device for evaluating the impact resistance in Examples and Comparative Examples.

A schematic diagram of a impact resistance testing device for the double-coated adhesive tape is shown in FIG. 2. The resulting double-coated adhesive tape was punched so that the outer size might be 45.7 mm in width and 60.7 mm in length and the inner size might be 44.3 mm in width and 59.3 mm in length, thus preparing a frame-shaped test piece having a width of 0.7 mm.

Next, as shown in FIG. 2 (a), a test piece 1 from which the release paper had been peeled off was stuck to a polycarbonate sheet 3 having a thickness of 2 mm and having a square hole having a width of 38 mm and a length of 50 mm in the center portion thereof so that the square hole might be located substantially at the center. Then, a polycarbonate sheet 2 having a width of 55 mm, a length of 65 mm, and a thickness of 1 mm was stuck from the top of the test piece 1 so that the test piece 1 might be located substantially at the center, thus assembling a testing device.

Subsequently, a pressure of 5 kgf was applied for 10 seconds from the side of the polycarbonate sheet located on top of the testing device to adhere by pressure the polycarbonate sheet and the test piece located up and down, and the laminate was allowed to stand at ordinary temperature for 24 hours.

(Determination of Impact Resistance)

As shown in FIG. 2 (b), the prepared testing device was turned over and fixed to a support, and an iron ball 4 having a weight of 300 g which has a size that passes through the square hole was dropped passing through the square hole. The height from which the iron ball is dropped was gradually increased, and the height from which the iron ball was dropped was measured when the test piece was peeled off from the polycarbonate sheet by the impact applied by the drop of the iron ball, obtaining the results of "impact resistance [cm] at a width of 0.7 mm".

Example 1

A polyolefin resin composition, comprising 70 parts by mass of a linear low density polyethylene ["Kernel KF370" manufactured by Japan Polyethylene Corporation, density: 0.905 g/cm$^3$] as a polyolefin resin (A), 30 parts by mass of a linear low density polyethylene ["Affinity KC8852" manufactured by The Dow Chemical Company, density: 0.875 g/cm$^3$] as a polyolefin resin (B), 1.0 part by mass of azodicarbonamide as a blowing agent of heat decomposition type, 1.0 part by mass of zinc oxide as a decomposition temperature regulator, and 0.5 part by mass of 2,6-di-t-butyl-p-cresol as an antioxidant, was fed to an extruder, melt-kneaded at 130° C., and then extruded into a continuous sheet having a thickness of 240 mm.

Next, the both surfaces of the above continuous sheet of the polyolefin resin composition were irradiated with 5.0 Mrad of electron beams at an acceleration voltage of 500 kV to crosslink the polyolefin resin composition. Then, the resulting polyolefin resin composition was continuously sent into a blowing oven maintained at 250° C. with hot wind and an infrared heater to be heated and expanded into a foam sheet having a thickness of 350 mm.

The resulting foam sheet was continuously sent out from the blowing oven. Then, in the state where the temperature of the foam sheet was maintained so that both surfaces thereof had a temperature of 200 to 250° C., the foam sheet was stretched in the TD direction at a stretching ratio of 1.3, and at the same time, the foam sheet was stretched in the MD direction at a stretching ratio of 1.3 by taking up the foam sheet at a take-up rate higher than the infeed rate (feed rate) of the foam sheet into the blowing oven, thereby obtaining a polyolefin resin foam sheet of Example 1. The resulting polyolefin resin foam sheet was evaluated in accordance with the above evaluation methods, and the results are shown in Table 1. Note that the take-up rate of the foam sheet was adjusted taking the expansion in the MD direction by the foaming of the foam sheet itself into consideration.

Examples 2 to 4, Comparative Examples 1 to 7

Examples 2 to 4 and Comparative Examples 1 to 7 were performed in the same manner as in Example 1 except that the formulation of the polyolefin resin (A) and the polyolefin resin (B) was changed as shown in Tables 1 and 2, and the dose for crosslinking was adjusted so as to provide the degree of crosslinking in Tables 1 and 2.

Note that the details of the polyolefin resins (A) and (B) used in Examples will be shown below.

<Polyolefin Resin (A)>

A linear low density polyethylene which is an ethylene-1-hexene copolymer obtained using a metallocene polymerization catalyst ("Kernel KF370" manufactured by Japan Polyethylene Corporation, density: 0.905 g/cm$^3$, melting point (DSC method) Tm: 97° C.)

<Polyolefin Resin (B)>

A linear low density polyethylene which is an ethylene-1-octene copolymer obtained using a metallocene polymerization catalyst ("Affinity KC8852" manufactured by The Dow Chemical Company, density: 0.875 g/cm$^3$, melting point (DSC method) Tm: 66° C.)

TABLE 1

|  |  |  | Example 1 | Example 2 | Example 3 | Example 4 |
|---|---|---|---|---|---|---|
| Composition (parts by mass) |  | Polyolefin resin (A) | 70 | 70 | 70 | 70 |
|  |  | Polyolefin resin (B) | 30 | 30 | 30 | 30 |
|  |  | Weighted average resin density [g/cm$^3$] | 0.896 | 0.896 | 0.896 | 0.896 |
|  | Additives | Blowing agent of heat decomposition type | 1.0 | 2.0 | 2.0 | 2.0 |
|  |  | Decomposition temperature regulator | 1.0 | 1.0 | 1.0 | 1.0 |
|  |  | Antioxidant | 0.5 | 0.5 | 0.5 | 0.5 |
|  | Mass ratio [(A)/(B)] |  | 2.3 | 2.3 | 2.3 | 2.3 |
| Physical properties of foam sheet |  | Thickness [mm] | 0.20 | 0.20 | 0.14 | 0.09 |
|  |  | Density [g/cm$^3$] | 0.63 | 0.56 | 0.56 | 0.56 |
|  |  | Expansion ratio [cm$^3$/g] | 1.6 | 1.8 | 1.8 | 1.8 |
|  |  | Degree of crosslinking (gel fraction) [% by mass] | 30.8 | 42.2 | 37.7 | 40.5 |
|  | Strength at break [kPa] | MD | 19100 | 15900 | 16600 | 18800 |
|  |  | TD | 14200 | 11900 | 10500 | 12100 |
|  | Average cell size [µm] | MD | 109 | 70 | 80 | 60 |
|  |  | TD | 88 | 83 | 88 | 74 |
|  |  | MD/TD | 1.24 | 0.84 | 0.91 | 0.81 |
|  | Maximum cell size [µm] | MD | 223 | 181 | 183 | 209 |
|  |  | TD | 206 | 204 | 228 | 239 |
|  |  | MD/TD | 1.08 | 0.89 | 0.80 | 0.87 |
|  | TD strength at break/MD average cell size [kPa/µm] *1 |  | 130 | 170 | 131 | 202 |
|  | MD strength at break/TD average cell size [kPa/µm] *2 |  | 217 | 192 | 189 | 254 |
|  | Average value of *1 and *2 [kPa/µm] |  | 174 | 181 | 160 | 228 |
|  | TD strength at break/MD maximum cell size [kPa/µm] *3 |  | 64 | 66 | 57 | 58 |
|  | MD strength at break/TD maximum cell size [kPa/µm] *4 |  | 93 | 78 | 73 | 79 |
|  | Average value of *3 and *4 [kPa/µm] |  | 79 | 72 | 65 | 69 |
|  | 25% compressive strength [kPa] |  | 1750 | 770 | 730 | 690 |
|  | Interlaminar strength [kPa] |  | 8300 | 5400 | 4500 | 3700 |
|  | Withstand voltage properties [kV/0.7 mm] | MD | 8.7 | 9.5 | 9.0 | 8.7 |
|  |  | TD | >12 | 10.3 | 9.7 | 10.0 |
|  |  | Rating | 1 | 1 | 1 | 1 |
|  | Impact resistance [cm/0.7 mm] |  | 65 | 72 | 67 | 62 |

TABLE 2

| | | Comparative Example | | | | | | |
|---|---|---|---|---|---|---|---|---|
| | | 1 | 2 | 3 | 4 | 5 | 6 | 7 |
| Composition (parts by mass) | Polyolefin resin (A) | 100 | 100 | 100 | 100 | 100 | 70 | 70 |
| | Polyolefin resin (B) | 0 | 0 | 0 | 0 | 0 | 30 | 30 |
| | Weighted average resin density [g/cm$^3$] | 0.905 | 0.905 | 0.905 | 0.905 | 0.905 | 0.896 | 0.896 |
| Additives | Blowing agent of heat decomposition type | 1.0 | 1.5 | 1.7 | 1.5 | 2.0 | 1.7 | 1.7 |
| | Decomposition temperature regulator | 1.0 | 1.0 | 1.0 | 1.0 | 1.0 | 1.0 | 1.0 |
| | Antioxidant | 0.5 | 0.5 | 0.5 | 0.5 | 0.5 | 0.5 | 0.5 |
| | Mass ratio [(A)/(B)] | — | — | — | — | — | 2.3 | 2.3 |
| Physical properties of foam sheet | Thickness [mm] | 0.20 | 0.20 | 0.20 | 0.15 | 0.08 | 0.20 | 0.14 |
| | Density [g/cm$^3$] | 0.63 | 0.59 | 0.50 | 0.56 | 0.40 | 0.50 | 0.50 |
| | Expansion ratio [cm$^3$/g] | 1.6 | 1.7 | 2.0 | 1.8 | 2.5 | 2.0 | 2.0 |
| | Degree of crosslinking (gel fraction) [% by mass] | 19.2 | 19.9 | 21.6 | 20.5 | 19.0 | 27.9 | 32.8 |
| Strength at break [kPa] | MD | 18300 | 15600 | 13700 | 12500 | 10600 | 13300 | 12200 |
| | TD | 13400 | 10700 | 8600 | 9500 | 8800 | 9200 | 8500 |
| Average cell size [μm] | MD | 115 | 127 | 133 | 104 | 82 | 120 | 122 |
| | TD | 97 | 154 | 156 | 205 | 119 | 151 | 188 |
| | MD/TD | 1.19 | 0.82 | 0.85 | 0.51 | 0.69 | 0.79 | 0.65 |
| Maximum cell size [μm] | MD | 232 | 245 | 242 | 294 | 223 | 238 | 314 |
| | TD | 203 | 292 | 314 | 400 | 497 | 275 | 424 |
| | MD/TD | 1.14 | 0.84 | 0.77 | 0.73 | 0.45 | 0.87 | 0.74 |
| | TD strength at break/MD average cell size [kPa/μm] *1 | 117 | 84 | 65 | 91 | 107 | 77 | 70 |
| | MD strength at break/TD average cell size [kPa/μm] *2 | 189 | 101 | 88 | 61 | 89 | 88 | 65 |
| | Average value of *1 and *2 [kPa/μm] | 153 | 93 | 77 | 76 | 98 | 83 | 68 |
| | TD strength at break/MD maximum cell size [kPa/μm] *3 | 58 | 44 | 36 | 32 | 39 | 39 | 27 |
| | MD strength at break/TD maximum cell size [kPa/μm] *4 | 90 | 53 | 44 | 31 | 21 | 48 | 29 |
| | Average value of *3 and *4 [kPa/μm] | 74 | 49 | 40 | 32 | 30 | 44 | 28 |
| | 25% compressive strength [kPa] | >2000 | 1300 | 880 | 480 | 86 | 720 | 310 |
| | Interlaminar strength [kPa] | 8700 | 6500 | 3800 | 3100 | 1200 | 4100 | 2600 |
| Withstand voltage properties [kV/0.7 mm] | MD | 8.5 | 7.5 | 7.0 | 6.2 | 6.5 | 6.8 | 6.3 |
| | TD | >12 | 8.5 | 8.0 | 5.5 | 5.0 | 8.3 | 5.2 |
| | Rating | 1 | 2 | 2 | 2 | 2 | 2 | 2 |
| | Impact resistance [cm/0.7 mm] | 60 | 55 | 43 | 35 | 27 | 48 | 31 |

As apparent from the results described above, the present invention can provide a thin polyolefin resin foam sheet which is excellent in impact-absorbing properties and impact resistance and has withstand voltage properties.

The invention claimed is:

1. A polyolefin resin foam sheet having a plurality of cells which is formed by foaming a polyolefin resin composition, wherein the polyolefin resin composition contains a polyolefin resin (A) and a polyolefin resin (B), and the weighted average resin density of the polyolefin resin (A) and the polyolefin resin (B) is 0.900 g/cm$^3$ or less; and
wherein, in the polyolefin resin foam sheet, a ratio of strength at break in the TD direction to the maximum cell size in the MD direction, [TD strength at break/MD maximum cell size], and a ratio of strength at break in the MD direction to the maximum cell size in the TD direction, [MD strength at break/TD maximum cell size], are both 45 kPa/μm or more,
wherein the polyolefin resin (A) is one or more selected from the group consisting of polyolefin resins having a density of 0.900 g/cm$^3$ or more, and the polyolefin resin (B) is one or more selected from the group consisting of polyolefin resins having a density of less than 0.900g/cm$^3$,
wherein both the polyolefin resin (A) and the polyolefin (B) are a poly ethylene resin.

2. The polyolefin resin foam sheet according to claim 1, wherein an average value of the ratio [TD strength at break/MD maximum cell size] and the ratio [MD strength at break/TD maximum cell size] is 50 kPa/μm or more.

3. The polyolefin resin foam sheet according to claim 1, wherein the polyolefin resin foam sheet is crosslinked.

4. The polyolefin resin foam sheet according to claim 1, wherein a mass ratio of the polyolefin resin (A) to the polyolefin resin (B), [(A)/(B)], is 0.20 to 10.

5. The polyolefin resin foam sheet according to claim 1, wherein the polyethylene resin is polymerized with a metallocene polymerization catalyst.

6. An adhesive tape having a pressure sensitive adhesive layer provided on at least one surface of the polyolefin resin foam sheet according to claim 1.

* * * * *